(12) United States Patent
Penzimer et al.

(10) Patent No.: US 12,226,133 B2
(45) Date of Patent: Feb. 18, 2025

(54) ORTHOPEDIC PLATE WITH MODULAR PEG AND COMPRESSION SCREW

(71) Applicant: EXTREMITY MEDICAL LLC, Parsippany, NJ (US)

(72) Inventors: Raymond Penzimer, Parsippany, NJ (US); Holman Chan, Parsippany, NJ (US); William James, Parsippany, NJ (US); Vladimir Sherman, Parsippany, NJ (US)

(73) Assignee: EXTREMITY MEDICAL LLC, Parsippany, NJ (US)

( * ) Notice: Subject to any disclaimer, the term of this patent is extended or adjusted under 35 U.S.C. 154(b) by 34 days.

(21) Appl. No.: 18/358,039

(22) Filed: Jul. 25, 2023

(65) Prior Publication Data
US 2024/0000489 A1 Jan. 4, 2024

Related U.S. Application Data

(63) Continuation of application No. 17/027,724, filed on Sep. 22, 2020, now Pat. No. 11,707,305, which is a
(Continued)

(51) Int. Cl.
*A61B 17/72* (2006.01)
*A61B 17/17* (2006.01)
(Continued)

(52) U.S. Cl.
CPC ...... *A61B 17/7225* (2013.01); *A61B 17/1775* (2016.11); *A61B 17/68* (2013.01);
(Continued)

(58) Field of Classification Search
CPC ............ A61B 17/7225; A61B 17/7233; A61B 17/7241; A61B 17/725; A61B 17/80; A61B 17/8004; A61B 17/8014
(Continued)

(56) References Cited

U.S. PATENT DOCUMENTS

| 4,936,844 A | 6/1990 | Chandler |
| 6,123,709 A | 9/2000 | Jones |

(Continued)

FOREIGN PATENT DOCUMENTS

| DE | 102006000948 | 10/2006 |
| FR | 2861576 | 5/2005 |

(Continued)

OTHER PUBLICATIONS

Patent Corporation Treaty—Application PCT/US2023/010070; International Search Report & Written Opinion, May 8, 2023.
(Continued)

*Primary Examiner* — Eduardo C Robert
*Assistant Examiner* — Christina Negrellirodriguez
(74) *Attorney, Agent, or Firm* — Kelley Drye & Warren LLP; Alan D. Gardner

(57) ABSTRACT

Assemblies and methods for fixation of bone or bone fragments using an orthopedic plate, a modular peg, and a compression screw. The modular peg is screwed into one of the apertures of the orthopedic plate. The modular peg may include an aperture having screw threads designed to receive the threads of the compression screw and serve as an anchor for the compression screw. By rotating the compression screw in relation to the modular peg, the compression screw may advance through the aperture of the modular peg, drawing the head of the screw toward the modular peg, and compressing the bone or bone fragments.

19 Claims, 14 Drawing Sheets

Related U.S. Application Data continuation of application No. 15/947,661, filed on Apr. 6, 2018, now Pat. No. 10,779,867.

(60) Provisional application No. 62/649,330, filed on Mar. 28, 2018, provisional application No. 62/482,552, filed on Apr. 6, 2017.

(51) Int. Cl.
  *A61B 17/68* (2006.01)
  *A61B 17/80* (2006.01)
  *A61B 17/86* (2006.01)
  *A61B 17/064* (2006.01)
  *A61F 2/30* (2006.01)
  *A61F 2/42* (2006.01)

(52) U.S. Cl.
  CPC ...... *A61B 17/7291* (2013.01); *A61B 17/8004* (2013.01); *A61B 17/8061* (2013.01); *A61B 17/8625* (2013.01); *A61B 17/0642* (2013.01); *A61B 2017/0645* (2013.01); *A61B 17/7233* (2013.01); *A61F 2002/3085* (2013.01); *A61F 2/4225* (2013.01)

(58) Field of Classification Search
  USPC ................. 606/62–64, 96, 105, 280–282
  See application file for complete search history.

(56) References Cited

U.S. PATENT DOCUMENTS

| | | | |
|---|---|---|---|
| 6,139,550 A | 10/2000 | Michelson | |
| 6,527,775 B1 | 3/2003 | Warburton | |
| 6,669,700 B1 | 12/2003 | Farris et al. | |
| 6,669,701 B2 | 12/2003 | Steiner | |
| 6,692,503 B2 | 2/2004 | Foley et al. | |
| 7,160,302 B2 | 1/2007 | Warburton | |
| 7,588,577 B2 | 9/2009 | Fend et al. | |
| 7,678,113 B2 | 3/2010 | Melkent | |
| 7,713,271 B2 | 5/2010 | Warburton | |
| 7,731,721 B2 | 6/2010 | Rathbun et al. | |
| 7,780,710 B2 | 8/2010 | Orbay | |
| 7,799,061 B2 | 9/2010 | Kay et al. | |
| 7,867,231 B2 | 1/2011 | Cole | |
| 7,914,532 B2 | 3/2011 | Shaver et al. | |
| 8,034,056 B2 | 10/2011 | Fencl et al. | |
| 8,092,453 B2 | 1/2012 | Warburton | |
| 8,100,910 B2 | 1/2012 | Warburton | |
| 8,100,953 B2 | 1/2012 | White | |
| 8,109,980 B2 | 2/2012 | Melkent | |
| 8,182,485 B1 | 5/2012 | Gonzalez-Hernandez | |
| 8,252,032 B2 | 8/2012 | White et al. | |
| 8,361,075 B2 | 1/2013 | Gonzalez-Hernandez | |
| 8,574,234 B2 | 11/2013 | Gonzalez-Hernandez | |
| 8,574,270 B2 | 11/2013 | Hess et al. | |
| 8,888,825 B2 | 11/2014 | Batsch | |
| 8,974,504 B2 | 3/2015 | Hess et al. | |
| 9,005,255 B2 | 4/2015 | Lewis et al. | |
| 9,017,329 B2 | 4/2015 | Tyber et al. | |
| 9,044,282 B2 | 6/2015 | Tyber et al. | |
| 9,066,768 B2 | 6/2015 | Weiner | |
| 10,779,867 B2* | 9/2020 | Penzimer | A61B 17/8625 |
| 11,707,305 B2* | 7/2023 | Penzimer | A61B 17/7225 |
| | | | 606/60 |
| 2003/0040748 A1 | 2/2003 | Aikins | |
| 2003/0060827 A1 | 3/2003 | Coughlin | |
| 2005/0015092 A1 | 1/2005 | Rathbun et al. | |
| 2005/0165395 A1 | 7/2005 | Orbay | |
| 2005/0171544 A1 | 8/2005 | Falkner | |
| 2005/0240190 A1 | 10/2005 | Gall | |
| 2005/0273101 A1 | 12/2005 | Schumacher | |
| 2006/0142763 A1 | 6/2006 | Munro et al. | |
| 2006/0173461 A1 | 8/2006 | Kay et al. | |
| 2006/0200143 A1 | 9/2006 | Warburton | |
| 2006/0241608 A1 | 10/2006 | Myerson et al. | |
| 2006/0264946 A1 | 11/2006 | Young | |
| 2007/0173835 A1 | 7/2007 | Medoff | |
| 2007/0225714 A1 | 9/2007 | Gradl | |
| 2007/0233114 A1 | 10/2007 | Bouman | |
| 2008/0091203 A1 | 4/2008 | Warburton et al. | |
| 2008/0132960 A1 | 6/2008 | Weaver et al. | |
| 2008/0300637 A1 | 12/2008 | Austin et al. | |
| 2009/0088804 A1 | 4/2009 | Kyle et al. | |
| 2009/0088806 A1 | 4/2009 | Leyden et al. | |
| 2009/0093849 A1 | 4/2009 | Grabowski | |
| 2009/0157077 A1 | 6/2009 | Larsen et al. | |
| 2009/0157079 A1 | 6/2009 | Warburton et al. | |
| 2009/0292292 A1 | 11/2009 | Fend et al. | |
| 2011/0046681 A1 | 2/2011 | Prandi et al. | |
| 2011/0137313 A1 | 6/2011 | Jensen et al. | |
| 2012/0083848 A1 | 4/2012 | Gonzalez-Hernandez | |
| 2012/0150240 A1 | 6/2012 | Medoff | |
| 2012/0226322 A1 | 9/2012 | Gonzalez-Hernandez | |
| 2013/0116734 A1 | 5/2013 | Gonzalez-Hernandez | |
| 2013/0238035 A1 | 9/2013 | Medoff | |
| 2015/0073486 A1 | 3/2015 | Marotta et al. | |
| 2016/0256204 A1 | 9/2016 | Patel | |
| 2018/0256218 A1 | 9/2018 | Steinlauf | |
| 2018/0310972 A1 | 11/2018 | Anding | |

FOREIGN PATENT DOCUMENTS

| | | |
|---|---|---|
| WO | 1994/02073 | 2/1994 |
| WO | 2006116164 | 11/2006 |
| WO | 2007131287 | 11/2007 |
| WO | 2008003433 | 1/2008 |
| WO | 2009120852 | 10/2009 |

OTHER PUBLICATIONS

Patent Corporation Treaty—Application PCT/US2018/026953; International Search Report & Written Opinion, Jul. 6, 2018.
Omega3 System Hansson Twin Hook Operative Technique, Omega3, Stryker Corporation, 2006.

* cited by examiner

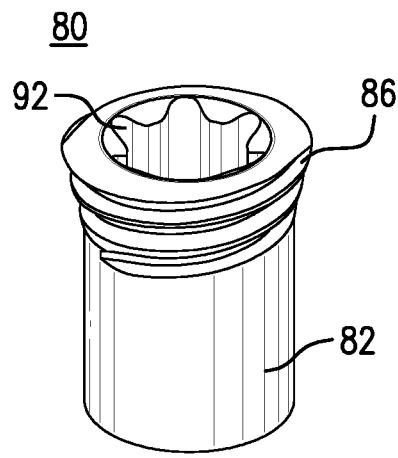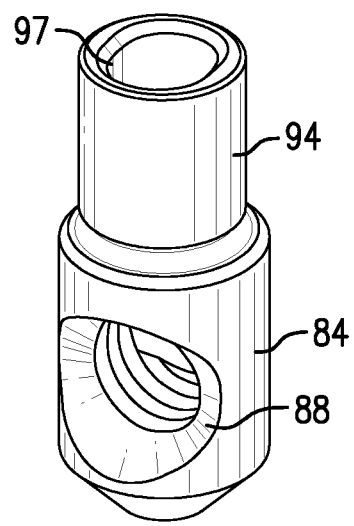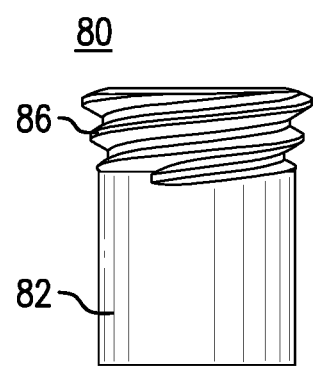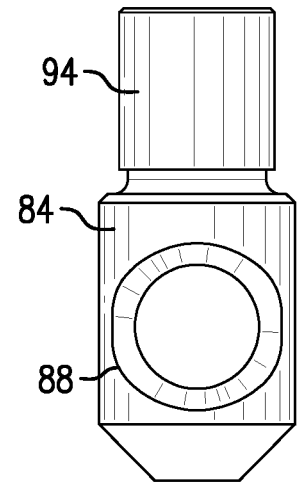
FIG.4BFIG.4C

ORTHOPEDIC PLATE WITH MODULAR PEG AND COMPRESSION SCREW

CROSS-REFERENCE TO RELATED APPLICATIONS

This application is a continuation of U.S. patent application Ser. No. 17/027,724, filed on Sep. 22, 2020, which is a continuation of U.S. patent application Ser. No. 15/947,661, filed on Apr. 6, 2018, which claims the benefit of Provisional Application No. 62/482,552, filed Apr. 6, 2017, and Provisional Application No. 62/649,330, filed Mar. 28, 2018, the entire contents of those applications are herein incorporated by reference.

FIELD OF THE INVENTION

This invention relates to the field of implant devices for bone fixation, and more particularly, to the combination of an orthopedic plate with a compression screw, using a modular peg as an anchor for the compression screw.

BACKGROUND OF THE INVENTION

Orthopedic plates are used to join two bones or bone fragments together, for example two adjoining phalangeal bones of the foot. Orthopedic plates typically have a plurality of apertures for receiving one or more screws or posts. The leading ends of the screws or posts may be inserted through one or more of the apertures and implanted into one of the bones or bone fragments. The plates and screws maintain the position and orientation of the bones or bone fragments and provide stabilization. One or more screws may be inserted into each bone. FIG. 1 shows an example of an orthopedic plate with a plurality of screws.

It may also be desirable to impart compression to the bone or bone fragments. Compression may be achieved by, for example, using one or more screws to join the bones or bone fragments. FIG. 2 discloses an example of screws used to compress two bones together. Assemblies of screws used to compress bones are also disclosed in prior patents such as U.S. Pat. Nos. 9,017,329 and 9,044,282, incorporated herein by reference.

In certain circumstances, it may be desirable to implant an orthopedic plate and also implant one or more compression screws. However, the screws used to attach the orthopedic plate to bones or bone fragments may, when implanted, occupy a portion or portions of the bones or bone fragments through which it may be preferable to implant the compression screws, thereby preventing the compression screws from being implanted at certain positions and/or angles. In addition, with certain prior art assemblies or apparatuses, it may be difficult to determine prior to implantation of a compression screw the extent to which a desired implant path for the screw will be blocked by one or more of the screws used to attach the plate.

A staple may also be used to compress two bones or bone fragments. However, commercially available orthopedic plates typically cover the joint between the two bones or bone fragments thereby reducing the exposed bone area into which the arms of a staple may be inserted.

Certain bone plates capable of providing compression in addition to stabilization have been developed. For example, U.S. Pat. No. 9,005,255 discloses an orthopedic plate with a compression housing that receives a compression screw. However, the angle at which the compression screw may be implanted is limited to a specific angle determined by the shape of the compression housing. Also, U.S. Pat. Nos. 8,574,270 and 8,974,504 disclose bone plates having multiple segments, and springs that provide a contractive force to compress the segments together. However, the construction of such multi-segment bone plates is complex and expensive, and the amount of compressive force they may generate is limited to the tensile force of the springs.

SUMMARY OF THE INVENTION

The present invention is directed to assemblies and methods for fixation of bones or bone fragments. The invention provides a novel way of combining the stabilization afforded by an orthopedic plate with the compressive force generated by a compression screw. A modular peg is inserted through one of the apertures of the orthopedic plate. The modular peg may include an aperture having screw threads designed to receive the threads of a compression screw. The modular peg may serve as an anchor for the compression screw. By rotating the compression screw in relation to the modular peg, the compression screw may advance through the aperture of the modular peg, drawing the head of the screw toward the modular peg, and thereby compressing the bone or bone fragments.

A modular peg in accordance with the present invention, without an orthopedic plate, may serve as an anchor for a compression screw. The modular peg may include an aperture having screw threads designed to receive the threads of a compression screw. Screw threads on the outer surface of the modular peg may facilitate implantation of the modular peg into bone and/or securing the modular peg to bone. As described above for the assembly including an orthopedic plate, by rotating the compression screw in relation to the modular peg, the compression screw may advance through the aperture of the modular peg, drawing the head of the screw toward the modular peg, and thereby compressing the bone or bone fragments.

Another object of the present invention is to provide a targeting guide for implanting a compression screw. The targeting guide may include a key insert designed to fit into an indentation of the modular peg. Inserting the key insert of the targeting guide into the indentation of the modular peg may ensure that the screw guide of the targeting guide is aligned with the aperture of the modular peg. The targeting guide may be rotated about the center axis of the modular peg, allowing the compression screw to be implanted at various angles in relation to the orthopedic plate and the joint between the bone or bone fragments to be compressed.

Another object of the present invention is to provide an orthopedic plate having a slot or cutout that allows a staple to be inserted therethrough. Each end of the staple may be inserted into one of the bone or bone fragments to be fixated. The staple may provide a compressive force to the bone or bone fragments. The staple may be used with or instead of the modular peg and compression screw described above.

BRIEF DESCRIPTION OF THE DRAWINGS

A further understanding of the invention can be obtained by reference to embodiments set forth in the illustrations of the accompanying drawings. Although the illustrated embodiments are merely exemplary of systems, methods, and apparatuses for carrying out the invention, both the organization and method of operation of the invention, in general, together with further objectives and advantages thereof, may be more easily understood by reference to the drawings and the following description. Like reference numbers generally refer to like features (e.g., functionally similar and/or structurally similar elements).

The drawings are not necessarily depicted to scale; in some instances, various aspects of the subject matter disclosed herein may be shown exaggerated or enlarged in the drawings to facilitate an understanding of different features. Also, the drawings are not intended to limit the scope of this invention, which is set forth with particularity in the claims as appended hereto or as subsequently amended, but merely to clarify and exemplify the invention.

FIGS. 4A-4C depict modular pegs in accordance with an embodiment of the present invention;

DETAILED DESCRIPTION OF THE INVENTION

The invention may be understood more readily by reference to the following detailed descriptions of embodiments of the invention. However, techniques, systems, and operating structures in accordance with the invention may be embodied in a wide variety of forms and modes, some of which may be quite different from those in the disclosed embodiments. Also, the features and elements disclosed herein may be combined to form various combinations without exclusivity, unless expressly stated otherwise. Consequently, the specific structural and functional details disclosed herein are merely representative. Yet, in that regard, they are deemed to afford the best embodiment for purposes of disclosure and to provide a basis for the claims herein, which define the scope of the invention. It must be noted that, as used in the specification and the appended claims, the singular forms "a", "an", and "the" include plural referents unless the context clearly indicates otherwise.

Figure 1:
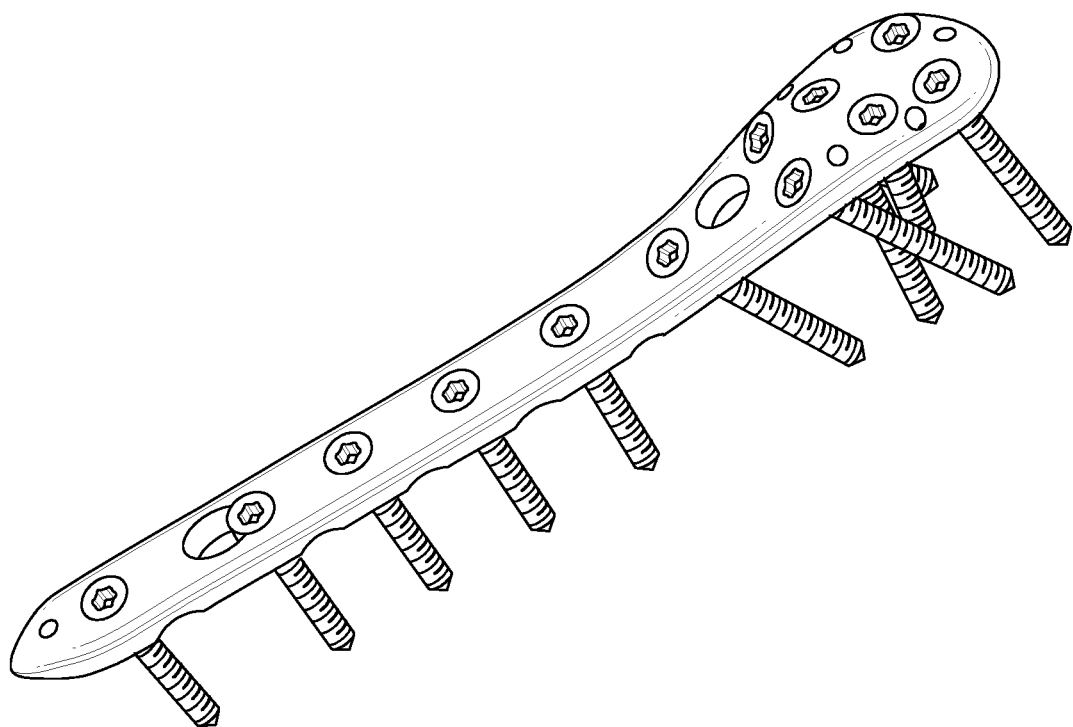
FIG. 1 depicts an example of existing bone plate and bone screws.
Figure 2:
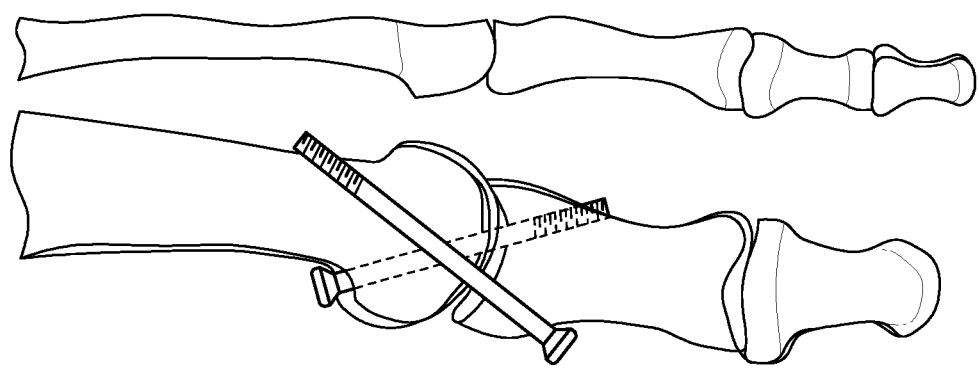
FIG. 2 depicts an example of existing compression screws.
Figure 3:
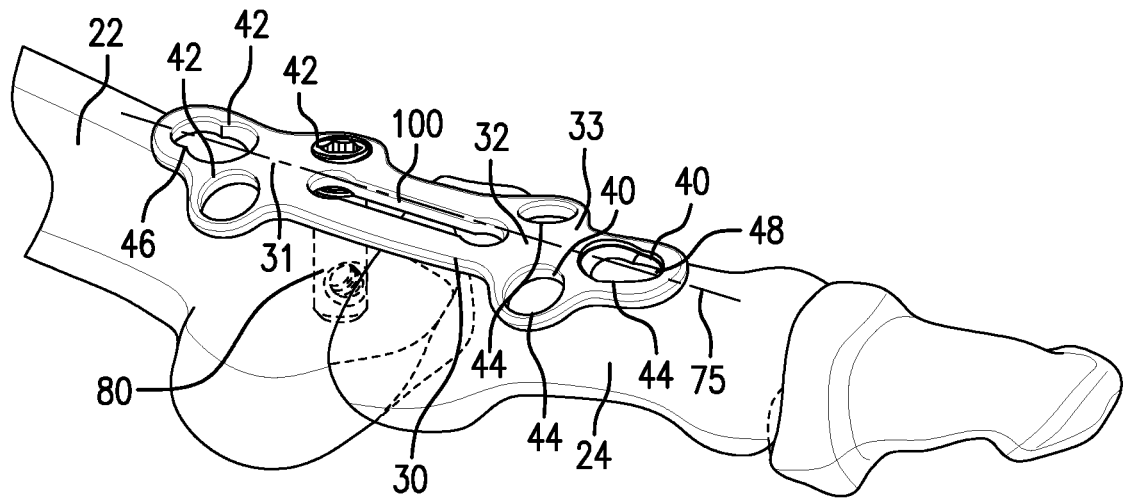
FIG. 3 depicts an orthopedic plate and modular peg in accordance with an embodiment of the present invention.

As shown in FIG. 3, orthopedic plate (30) may be implanted across the site where two or more bone or bone fragments (22, 24) meet. Orthopedic plate (30) has a bottom surface (34, not shown) that may make contact with one or more the bones or bone fragments, and a top surface (32). Top surface (32) of orthopedic plate (30) may have one or more apertures (40, 42, 44), each aperture (40, 42, 44) leading to a bore that extends from the aperture (40, 42, 44) to a corresponding aperture on the bottom surface (34). The center line of each bore may be perpendicular to top surface (32) and/or bottom surface (34). In the alternative, the center line of each bore may be set at an angle other than perpendicular to top surface (32) and/or bottom surface (34), for example, 5 degrees, 10 degrees, 15 degrees, 20 degrees, 25 degrees, 30 degrees, 35 degrees, 40 degrees, 45 degrees, or any other angle from perpendicular to top surface (32).

One or more apertures (42) may be situated over a first bone or bone fragment (22), and one or more apertures (44) may be situated over a second bone or bone fragment (24). Each aperture (40, 42, 44) may be circular or may be another shape, such as an oval, an elongated circle, or a rectangle having semi-circular ends. One or more apertures (40, 42, 44) at top surface (32), one or more of the apertures at bottom surface (34), and/or one or more bores may be tapered. In addition or in the alternative, one or more of the bores may be threaded.

The apertures of orthopedic plate (30) may be arranged in one or more clusters, which may be dictated by the shape of orthopedic plate (30) and/or the bones or bone fragments to be joined. Orthopedic plate (30) may have any shape, and top surface (32) and/or bottom surface (34) of orthopedic plate (30) may be curved or otherwise shaped to follow the contour of one or more of the bone or bone fragments that it is used to join. For example, as shown in FIG. 3, orthopedic plate (30) may have an elongated shape with a first plurality of apertures (42) arranged at a first end (31) of orthopedic plate (30) and a second plurality of apertures (44) arranged at a second end (33) of orthopedic plate (30). The distance between the closest point of each aperture in a cluster may be no more that the radius of the smallest aperture, or the diameter of the smallest aperture. The distance between the clusters as measured between the closest apertures (40) may be greater than a multiple of the diameter of one of the apertures (40).

Orthopedic plate (30) may be attached to first bone or bone fragment (22) and/or second bone or bone fragment (24) by one or more bone screws (50). Each bone screw (50) may be inserted through an aperture (40) and the corresponding bore in orthopedic plate (30) and implanted into a bone or bone fragment (22, 24) by, for example, rotating bone screw (50) so that the threads of bone screw (50) cause bone screw (50) to be screwed into bone or bone fragment (22, 24). The size and/or shape of each aperture (40) may be the same or substantially the same as the size and/or shape of the head or shaft of bone screw (50) to be inserted therein. The head of each bone screw may be tapered, bulbous, semispherical, cylindrical, or any other shape. The exterior surface of the screw head may be threaded. When each bone screw (50) is implanted into bone or bone fragment, the exterior surface of the head of bone screw (50) may abut the interior surface of the bore at aperture (40). Each bone screw (50) may thereby couple to orthopedic plate (30). In the alternative or in addition, the bore into which one or more of the bone screws (50) is inserted may have a threaded interior surface, and the exterior surface of the head of one or more bone screws (50) may be threaded. The threads on the exterior surface of the head of each bone screw may engage the threads on the interior surface of each bore.

In the alternative or in addition, one or more apertures (46, 48) may be elongated in a direction parallel to and/or in line with the longitudinal axis of the orthopedic plate. Longitudinal axis (75) of orthopedic plate (30) shown in FIG. 3 extends from the first end (31) to the second end (33). In addition or in the alternative, one or more apertures (not shown) may be elongated in a direction that is offset at an angle from longitudinal axis (75) of orthopedic plate (30). The angle may be, for example, less than degrees offset from longitudinal axis (75). The shape of apertures (46, 48) in FIG. 3 is that of an elongated circle.

A bone screw (50) inserted through an elongated aperture and implanted into bone or bone fragment (22, 24) may move in relation to orthopedic plate, for example along the longitudinal axis of the elongated aperture, as the bone or bone fragment (22, 24) in which the bone screw is implanted is compressed with another bone or bone fragment (22, 24).

Figure 7A:
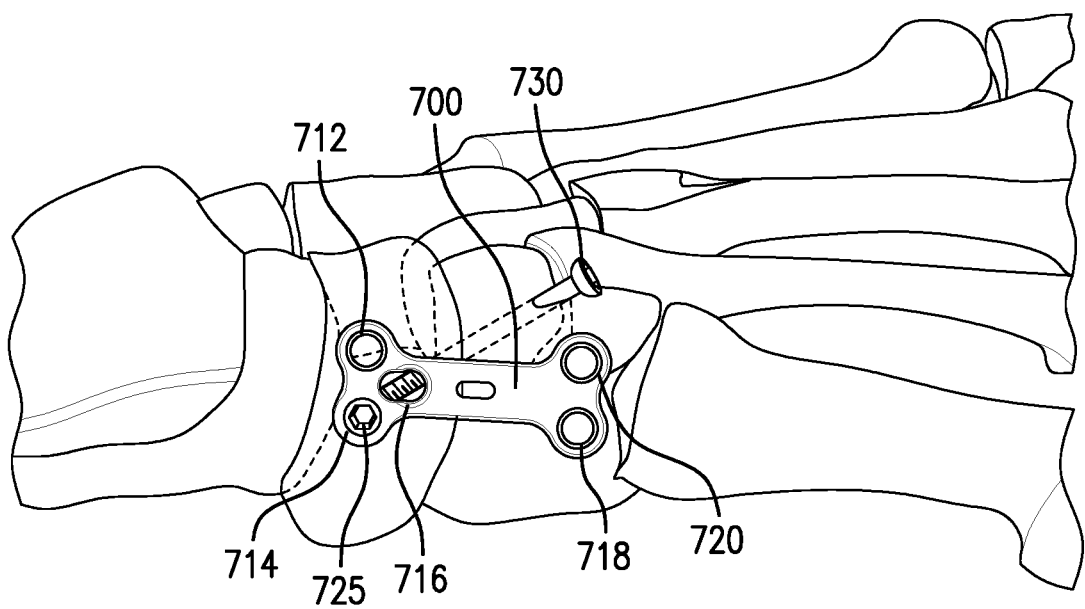
FIGS. 7A-7C depict alternate plate and screw configurations in accordance with the present invention.
Figure 7B:
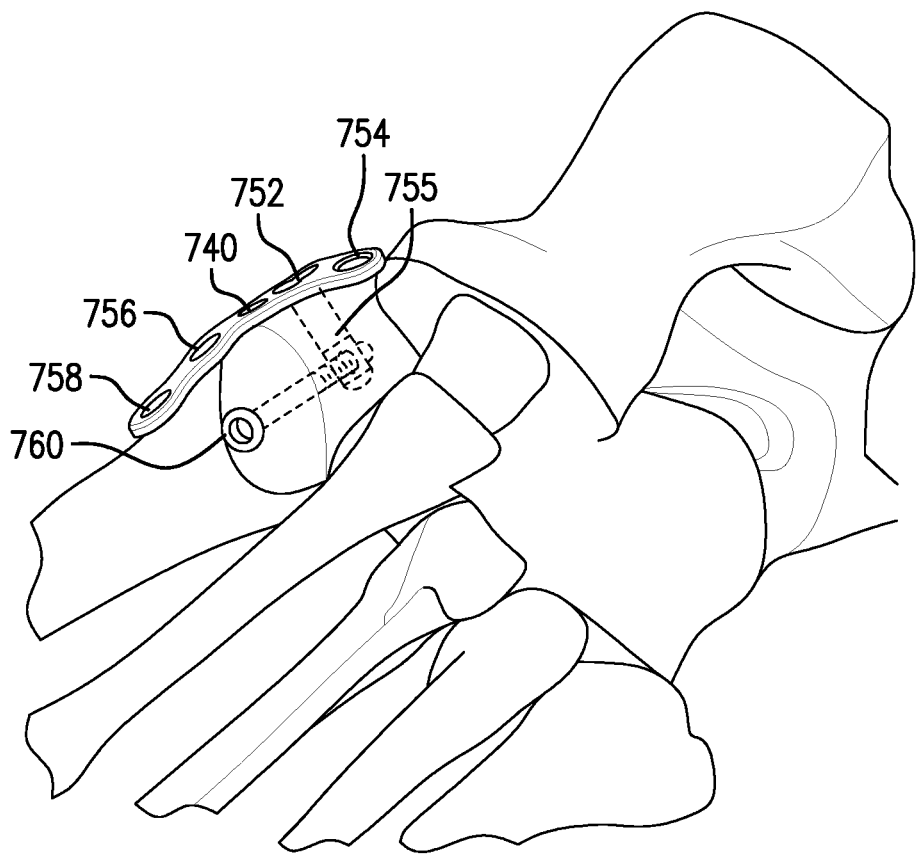
Figure 7C:
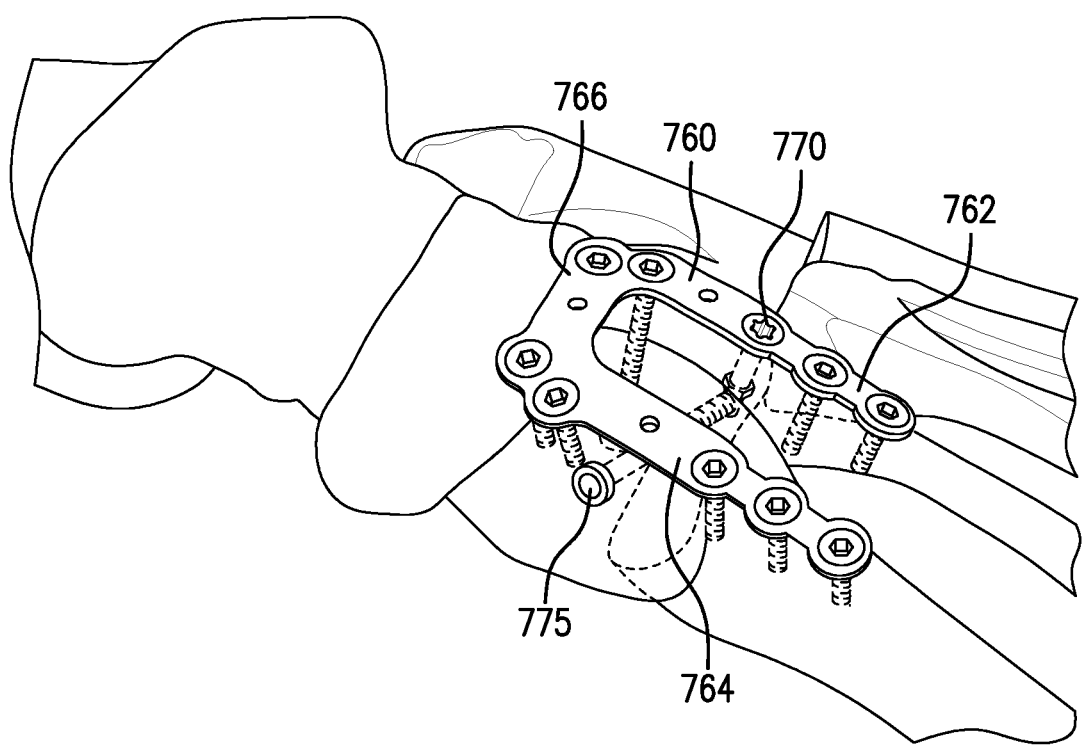

FIGS. 7A-7C depict other example embodiments of orthopedic plates and screw configurations in accordance with the present invention. FIG. 7A depicts an orthopedic plate (700) having three apertures (712, 714, 716) at a first end and two apertures (718, 720) at a second end. Aperture (716) is elongated along the longitudinal axis of orthopedic plate (700) and is tapered at the right side of the aperture. As depicted in FIG. 7A, a modular peg (725) is inserted in aperture (714) and compression screw (730) is engaged with modular peg (725).

FIG. 7B depicts an orthopedic plate (740) having two apertures (752, 754) at a first end and two apertures (756, 758) at a second end. Apertures (756, 758) are both aligned with the longitudinal axis of orthopedic plate (740). Orthopedic plate (740) is also curved to follow the contour of one or more of the bones for which it is used to join. Each aperture may receive a bone screw or a modular peg. As depicted in FIG. 7B, a modular peg (755) is inserted in aperture (752) and compression screw (760) is engaged with modular peg (755).

FIG. 7C depicts orthopedic plate (760) having a U-shape with a first arm (762) and second arm (764), joined by a bridge section (766). First arm (762) and second arm (764) each have a plurality of apertures that each may receive a bone screw or a modular peg. As depicted in FIG. 7C, a modular peg (770) is inserted in one of the apertures in first arm (762) and compression screw (775) is engaged with modular peg (755).

Orthopedic plate (30) may be used to join a proximal bone (22) and a distal bone (24) of the foot. Orthopedic plate (30) may be implanted by first placing orthopedic plate (30) over the site where proximal bone (22) and distal bone (24) are to be joined. A bone screw (50) may first be implanted in proximal bone (22) by inserting the bone screw (50) through an aperture (42) in the top surface (32) of orthopedic plate (30), through the corresponding bore leading to bottom surface (34) of orthopedic plate (30), and then screwing bone screw (50) into proximal bone (22). One or more additional bone screws (50) may then be implanted in proximal bone (22). After one or more bone screws (50) are implanted in proximal bone (22) thereby attaching orthopedic plate to proximal bone (22), a bone screw (50) may be implanted in distal bone (24) by inserting the bone screw (50) through an aperture (40) in the top surface (32) of orthopedic plate (30), through the corresponding bore leading to bottom surface (34) of orthopedic plate (30), and then screwing bone screw (50) into distal bone (24).

In the alternative, a bone screw (50) may first be implanted in distal bone (24) by inserting the bone screw (50) through an aperture (40) in the top surface (32) of orthopedic plate (30), through the corresponding bore leading to bottom surface (34) of orthopedic plate (30), and then screwing bone screw (50) into distal bone (24). One or more additional bone screws (50) may then be implanted in distal bone (24). After one or more bone screws (50) are implanted in distal bone (24) thereby attaching orthopedic plate to distal bone (24), a bone screw (50) may be implanted in proximal bone (22) by inserting the bone screw (50) through an aperture (42) in the top surface (32) of orthopedic plate (30), through the corresponding bore leading to bottom surface (34) of orthopedic plate (30), and then screwing bone screw (50) into proximal bone (22).

While one or more of the bone screws (50) are being implanted, the orthopedic plate may be provisionally pinned in place with pins. Each pin may be inserted through an aperture and into a bone or bone fragment (22, 24). A hole may first be drilled for each pin before the pin is inserted. A pin may be used to join the orthopedic plate to proximal bone (22) and/or a pin may be used to join the orthopedic plate to distal bone (24). When at least one bone screw (50) is implanted into proximal bone (22), a pin used to join the orthopedic plate to proximal bone (22) may be removed. When at least one bone screw (50) is implanted into distal bone (24), a pin used to join the orthopedic plate to distal bone (24) may be removed.

Each bone screw (50) may comprise a shaft extending from a first end to a second end along an axis. The first end may have a head (52). Head (52) may be tapered, bulbous or another shape. The outer surface of head (52) may have threads capable of mating with screw threads in aperture (40) of orthopedic plate (30). The second end of bone screw (50) may be threaded. The leading edge of bone screw (50) may comprise self-tapping threads.

As shown in FIG. 3, a peg may be inserted through an aperture (40) in orthopedic plate (30), through the corresponding bore, and into one of the bones or bone fragments (22, 24). Exemplary peg (80) is shown in FIG. 3. Threads on the exterior surface of the peg (80) may engage threads on the interior surface of the bore. In the alternative, peg (80) may first be implanted into bone or bone fragment (22, 24) by screwing peg (80) into the bone or bone fragment (22, 24) and/or by first drilling a hole in bone or bone fragment (22, 24). Orthopedic plate (30) may then be placed over the bones or bone fragments (22, 24) with peg (80) beneath bottom surface (34) of orthopedic plate (30) at the time that orthopedic plate (30) is placed. Peg (80) may then be rotated such that threads on the outer surface of peg (80) engage threads in a bore in orthopedic plate (30) and the upper portion of peg (80) is inserted through the bore from beneath orthopedic plate (30).

In the alternative, a peg may be attached to orthopedic plate (30) by other means, including by press fitting or by snapping. In the alternative, a separate component, such as a cap (not shown), may be used to attached the top end of peg (80) to orthopedic plate (30).

A plurality of pegs may be coupled to orthopedic plate (30), each peg inserted through one of the apertures (40) in orthopedic plate (30). For example, a plurality of pegs may be inserted through apertures (40) in orthopedic plate (30) and into one of the bones or bone fragments (22, 24). In another embodiment, at least one peg (80) may be inserted through an aperture (40) in orthopedic plate (30) and into proximal bone (22), and at least one peg (80) may be inserted through an aperture (40) in orthopedic plate (30) and into distal bone (24).

In each embodiment disclosed herein, when a peg (80) is implanted to its final position, no portion of peg (80) extends above top surface (32) of orthopedic plate (30).

Figure 4A:
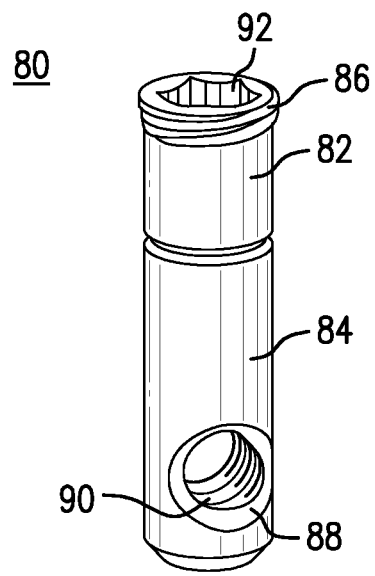
Figure 5:
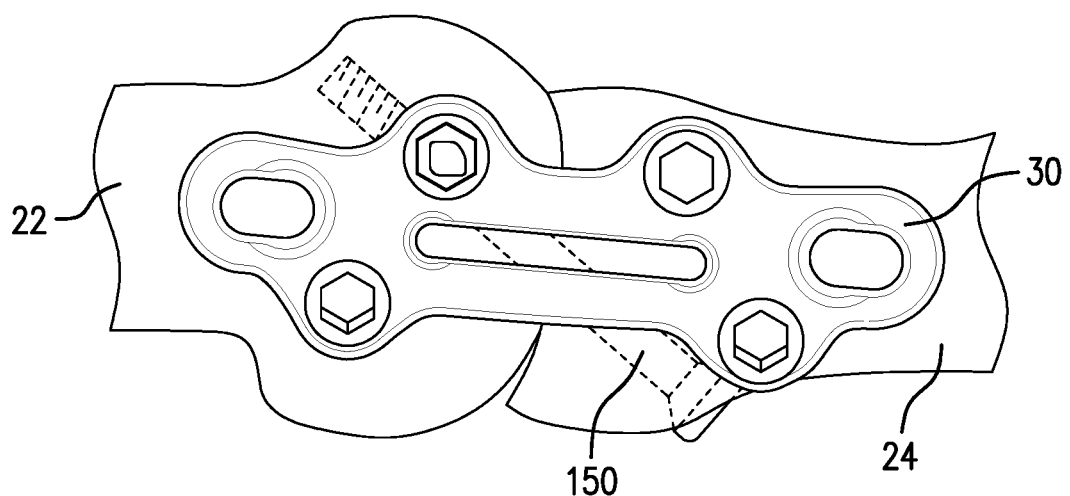
FIG. 5 depicts an assembly of an orthopedic plate, a modular peg, and a compression screw in accordance with an embodiment of the present invention.

Each peg may extend from a top end to a bottom end, with a longitudinal axis extending from the center of the top end to the center of the bottom end. The peg may be one solid form, or may be comprised of two portions joined together as shown, for example, by modular peg (80) in FIGS. 4A-4C. The peg may be cylindrical, may have a square cross-section, a rectangular cross-section, an oval cross-section, a triangular cross-section, or any other shaped cross-section. The peg may also have multiple cross sections between the top portion and the bottom portion of the peg. If the peg has a top portion and a bottom portion, the portions may have the same cross-section, or may have different cross-sections—different shapes, different sizes, or both. The peg may also be tapered so as to be wider at the top end than the bottom end, or so as to be wider at the bottom end than the top end. The peg may also have one or more cutouts along the outer surface of the peg. The cutouts may serve to reduce the weight of the peg, or to allow for bone to grow therein to secure the peg to a bone or bone fragment (22, 24).

Each peg may have one or more apertures. A bore may extend transversely from each aperture partially or completely through the peg. Each bore may be fully threaded, may have no threads, or may be threaded for a portion of the length of the bore and have no threads for the remainder of the length of the bore. The center axis of each bore may intersect the longitudinal axis of the peg at a perpendicular angle or at an angle offset from a perpendicular angle.

If the peg includes a plurality of bores, each bore may have the same diameter, or the bores may have different diameters. If a peg has more than one bore, the center axis of each bore may be parallel with each other, or may be offset at one or more angles.

The top end of each peg may include a first set of screw threads on the outer surface capable of mating with screw threads on the inner surface of a bore of orthopedic plate (30). The outer surface of the bottom end of each peg may have screw threads capable of engaging the bone or bone fragment (22, 24). The screw threads at the bottom end of each peg may be self-tapping threads. The bottom end of each peg may be tapered to further facilitate screwing the peg into bone fragment (22, 24).

FIGS. 4A-4C and 9A-9B depict exemplary modular pegs (80) in accordance with the present invention. Modular peg (80) has a top portion (or first portion) (82) and a bottom portion (or second portion) (84). Top portion (82) and bottom portion (84) may be rotatably connected. Top portion (82) and bottom portion (84) may be snapped together, screwed together, swaged, joined together with a ball bearing or with a pin and caliper, or by other means.

As noted above, top portion (82) may include screw threads (86) capable of mating with screw threads on the inner surface of a bore in orthopedic plate (30). Threads (86) may extend from at or near the top end of top portion (82) along the outer surface of top portions (82) for a distance equal to or approximately equal to the thickness of orthopedic plate (30) or the length of the bore into which it is to be inserted. Threads (86) or a second thread (not shown) may extend partially or fully along the remaining outer surface of top portion (82) and may engage a bone or bone fragment (22, 24) when modular peg is implanted. The threads partially or fully along the remaining outer surface of top portion (82) may have a smaller outer diameter than the threads at the top end of top portion (82), to facilitate inserting peg (80) through a bore in orthopedic plate (30).

Bottom portion (84) of modular peg (80) may have screw threads (not shown) extending along part of or along the entirety of its outer surface. The screw threads may engage the bone or bone fragment (22, 24). The screw threads may be self-tapping threads. The bottom end of modular peg (80) may be tapered to further facilitate screwing modular peg (80) into bone fragment (22, 24). The taper may also be threaded, and the threads may be self-tapping.

The top end of top portion (82) may include aperture (92) that is capable of receiving a tool (not shown) to facilitate mating screw threads (86) of top portion (82) with screw thread in a bore of orthopedic plate (30), or to facilitate screwing modular peg (80) into bone or bone fragment (22, 24). Aperture (92) may have a star shape, a triangular shape, a hexagonal shape, or any other shape to which the tool may be applied. The tool may have the same or similar shape as the shape of aperture (92).

Top portion (82) and bottom portion (84) may each include one or more apertures (88). Aperture (88) may be tapered. A transverse bore may extend transversely from each aperture (88) partially or completely through modular peg (80). Each transverse bore may be fully threaded with screw threads (90), may have no threads, or may be threaded for a portion of the length of the bore and have no threads for the remainder of the length of the bore. The center axis of each transverse bore may intersect the longitudinal axis of modular peg (80) at a perpendicular angle or at an angle offset from a perpendicular angle.

Figure 9A:
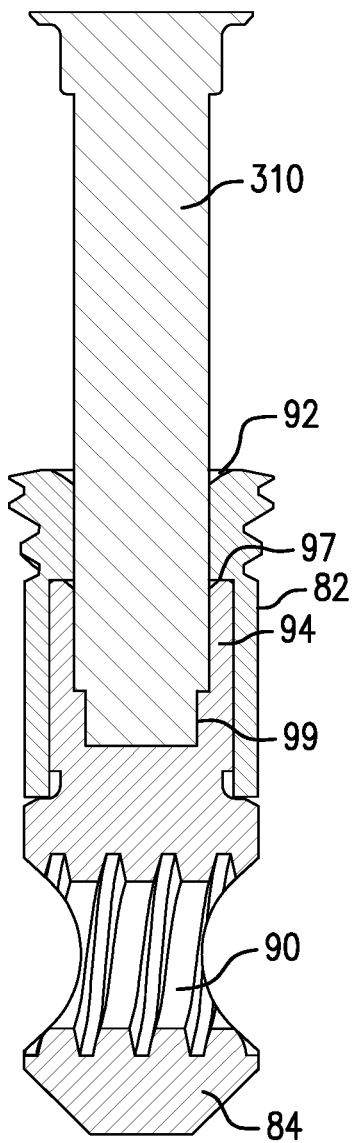
FIGS. 9A and 9B depict cut away views of a key insert of a compression screw targeting guide inserted in a modular peg in accordance with an embodiment of the present invention.
Figure 9B:
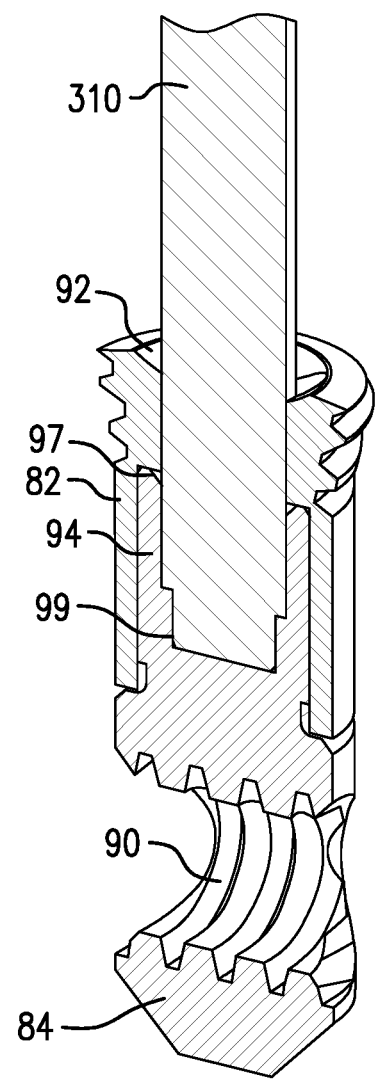

A key member (94) of bottom portion (84) may extend above the site where the bottom end of the bottom portion (84) and the top portion (82) meet, and into top portion (82). As shown in FIG. 4B, an aperture (97) at the top of key member (94) may have a particular shape meant to receive a key insert of a targeting guide. The shape of aperture (97) may be a diamond, a square, an oval, an elongated circle, a star, or any other shape. In addition or in the alternative, as shown in FIGS. 9A and 9B, aperture (97) of key member (94) may lead to a cavity within key member (94). At the bottom of the cavity may be indentation (99). Indentation (99) may have the same shape as aperture (97) or may have a different shape. For example, the shape of indentation (99) may be a diamond, a square, an oval, an elongated circle, a star, or any other shape. Indentation (99) may be the same size as aperture (97), or as shown in FIGS. 9A and 9B, indentation (99) may have a smaller size than aperture (97). In addition or in the alternative, the exterior wall or walls of key member (94) may form the shape of a diamond, a square, an oval, an elongated circle, or a star.

One or more of the points or other shape features of key member (94), aperture (97), and/or indentation (99) may align with aperture (88) and/or the center axis of a transverse bore through bottom portion (84). In addition, or in the alternative, key member (94) may include one or more markings indicating the orientation of aperture (88) and/or the center axis of a transverse bore through bottom portion (84).

Figure 6:
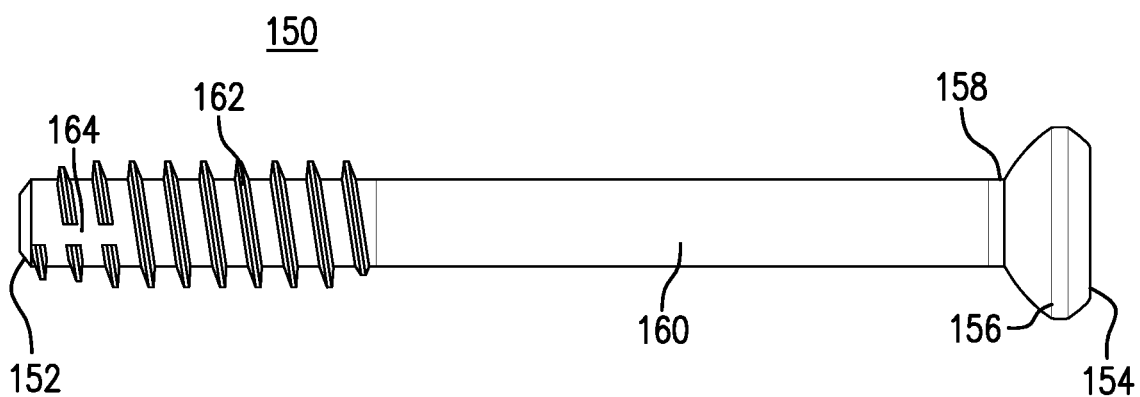
FIG. 6 depicts a compression screw.

As depicted in FIGS. 5, 7A-7C, and 10A, a compression screw (150) may be inserted through one bone or bone fragment (22), into a second bone or bone fragment (24), and join with a peg or modular peg (80). FIG. 6 depicts an exemplary compression screw (150) that may have a first end (152) and a second end (154). Second end (154) may have a screw head (156). Screw head (156) may be tapered, bulbous, semispherical, cylindrical, or another shape. The exterior surface of screw head (156) may be threaded. In the alternative, compression screw (150) may not have a screw head (156).

A shaft (160) may run from the bottom end (158) of screw head (156) to the first end (152) of compression screw (150). If compression screw (150) does not have a screw head, then the shaft (160) may run from first end (152) to second end (154). Some or all of shaft (160) may be threaded with screw threads (162). First end (152) of compression screw (150) may be truncated and/or may have a self-tapping screw thread (164). Compression screw (150) may be cannulated to receive, for example, a K-wire.

Figure 8A:
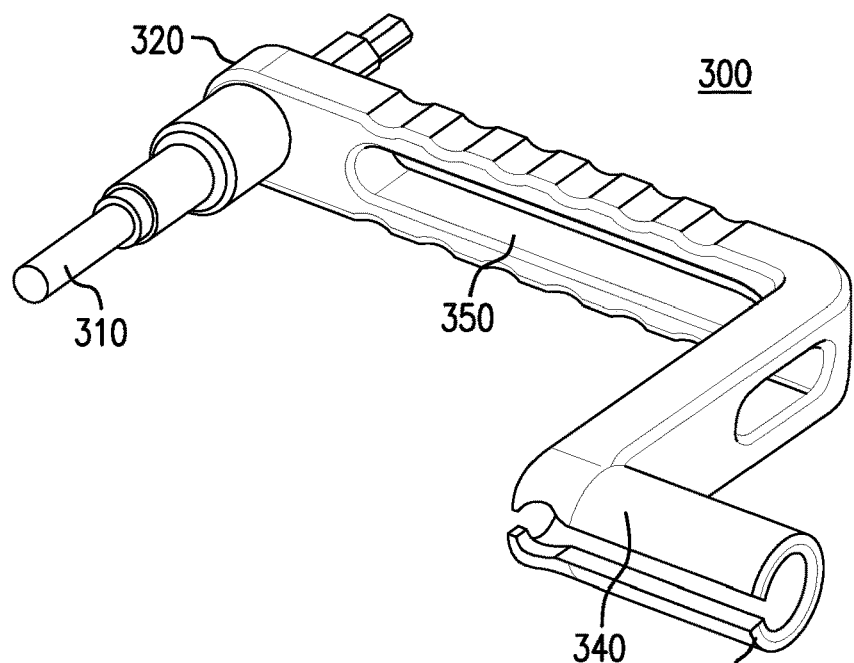
FIG. 8A depicts a compression screw targeting guide in accordance with an embodiment of the present invention.

As shown in FIGS. 8-10, a targeting guide (300) may be used to implant compression screw (150). Targeting guide (300) may have a key insert (310) at a first end (320) and a screw guide (340) at a second end (330). First end (320) and second end (330) of targeting guide (300) may be connected by bridge (350).

Figure 8B:
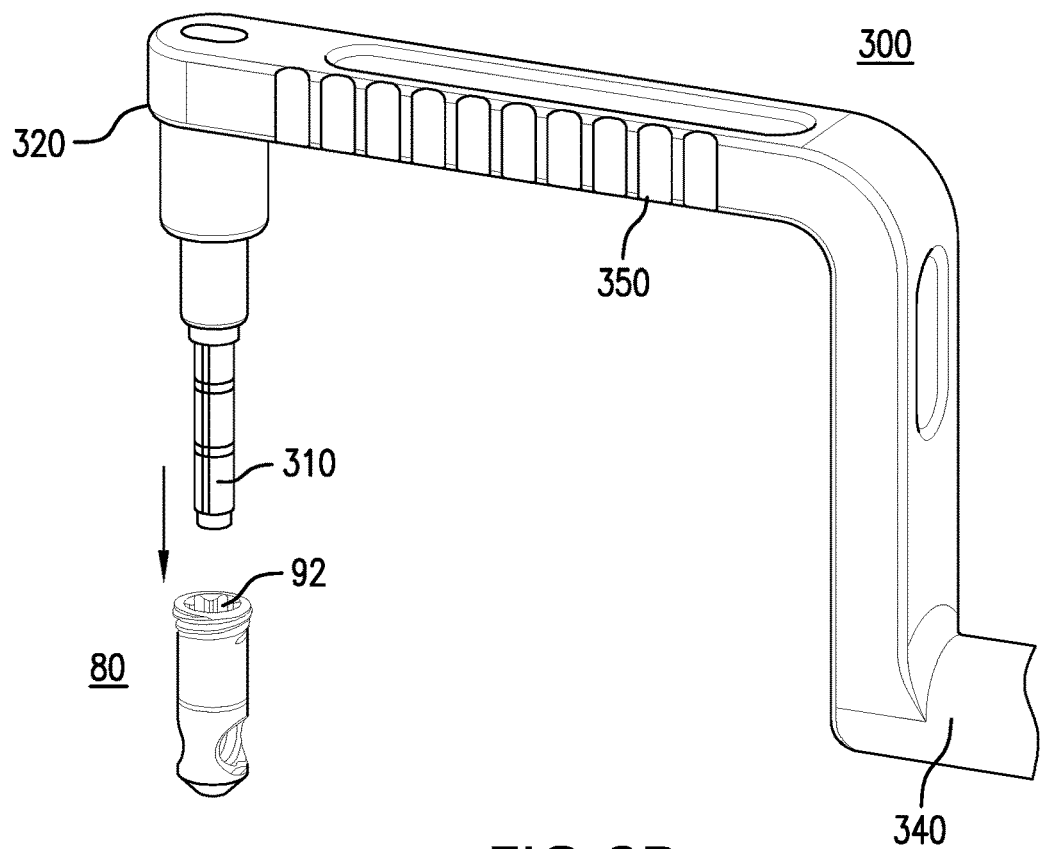
FIG. 8B depicts a compression screw targeting guide and a modular peg in accordance with an embodiment of the present invention.

As shown in FIGS. 8B, 9A and 9B, key insert (310) of targeting guide (300) may be inserted into aperture (92) of modular peg (80). Key insert (310) may have the same shape and may be inserted into aperture (97) and/or indentation (99) of modular peg (80). Inserting key insert (310) of targeting guide (300) into indentation (99) may cause the longitudinal axis of screw guide (340) to align with aperture (88) of the bottom portion (84) of modular peg (80). In the alternative, key insert (310) may have an aperture that fits over key member (94). Attaching key insert (310) of targeting guide (300) over key member (94) cause the longitudinal axis of screw guide (340) to align with aperture (88) of the bottom portion (84) of modular peg (80).

Figure 10A:
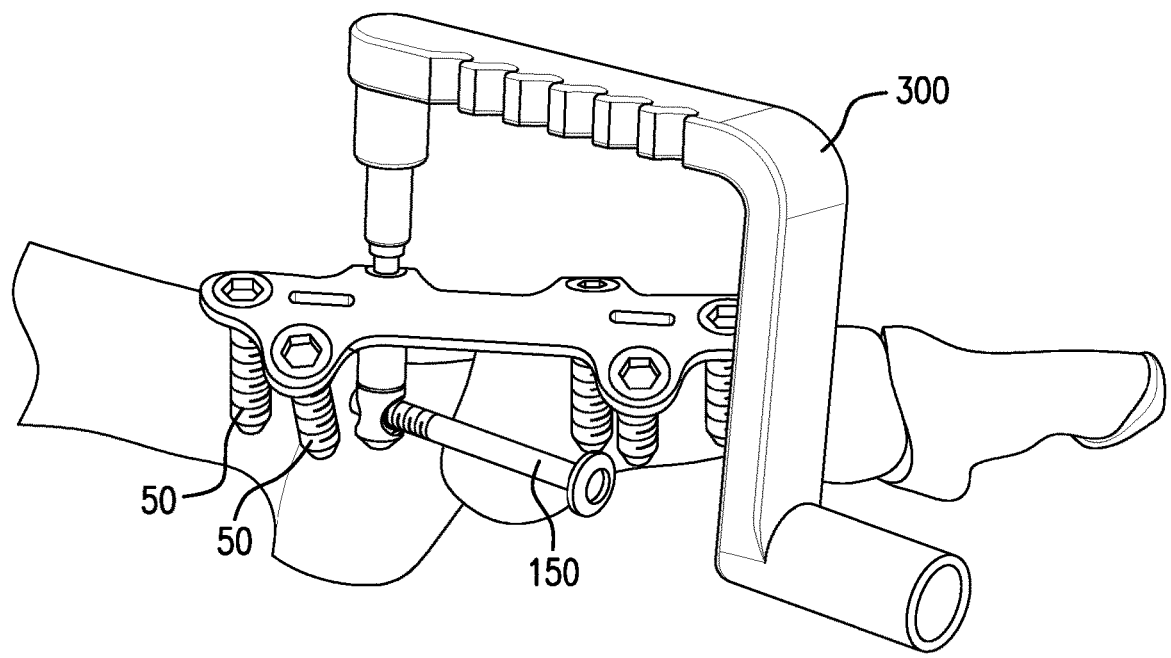
FIG. 10A depicts an assembly of an orthopedic plate, a modular peg, and a compression screw with a compression screw targeting guide in accordance with an embodiment of the present invention.
Figure 10B:
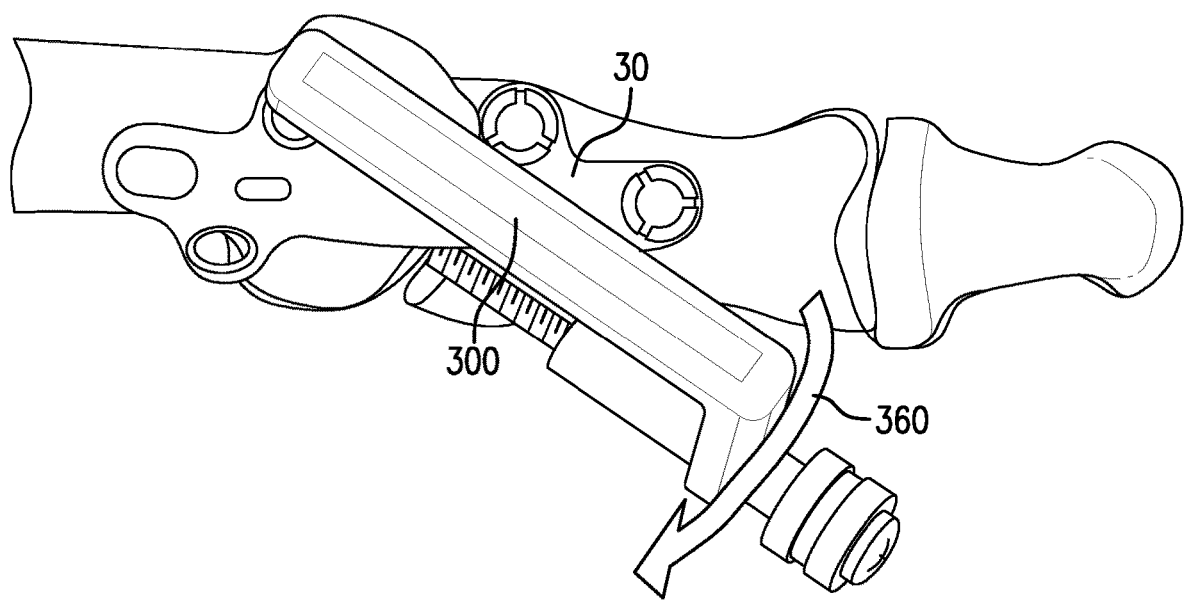
FIG. 10B depicts an assembly of an orthopedic plate, a modular peg, and a targeting guide in accordance with an embodiment of the present invention.

Also, as shown in FIG. 10B, rotating targeting guide (300) about the center axis of modular peg (80) may allow the compression screw to be implanted at various angles in relation to orthopedic plate (30) and/or the joint between the bone or bone fragments to be compressed. As shown in FIG. 10B, if key insert (310) is matched to and engages with aperture (97) and/or indentation (99), rotating targeting guide (300) by a certain angle (360) in one direction may cause bottom portion (84) of modular peg (80) to rotate the same angle (360) in the same direction, thereby maintaining the alignment of screw guide (340) with aperture (88) and the center axis of the transverse bore through bottom portion (84) of modular peg (80). Maintaining alignment of screw guide (340) with aperture (88) ensures that first end (152) of compression screw (150) will pass through aperture (88) when compression screw (150) is implanted. Having the capacity to vary the angle at which compression screw (150) may be implanted allows the optimal angle to be chosen for bone fixation.

A drill guide (not shown) may be added to the screw guide to facilitate drilling a hole for a compression screw. A wire guide may be added to the screw guide or to the drill guide to facilitate insertion of a guidewire. The compression screw may be cannulated and may be implanted using the guidewire.

If a plurality of pegs or modular pegs (80) are used with orthopedic plate (30), the distance between bottom surface (34) of orthopedic plate (300) and the center axis of each aperture (88) may be varied for each modular peg (80) to vary the height at which each compression screw (150) is implanted so that they do not make contact with each other. Preferably, to use the same targeting guide (300) to install each compression screw (150), as the distance between the center axis of each aperture (88) and the bottom surface of plate (30) varies, the depth of indentation (99) and/or the height of key member (94) may also vary by the same distance to ensure that the screw guide (340) aligns each compression screw (150) with each aperture (88).

Figure 11:
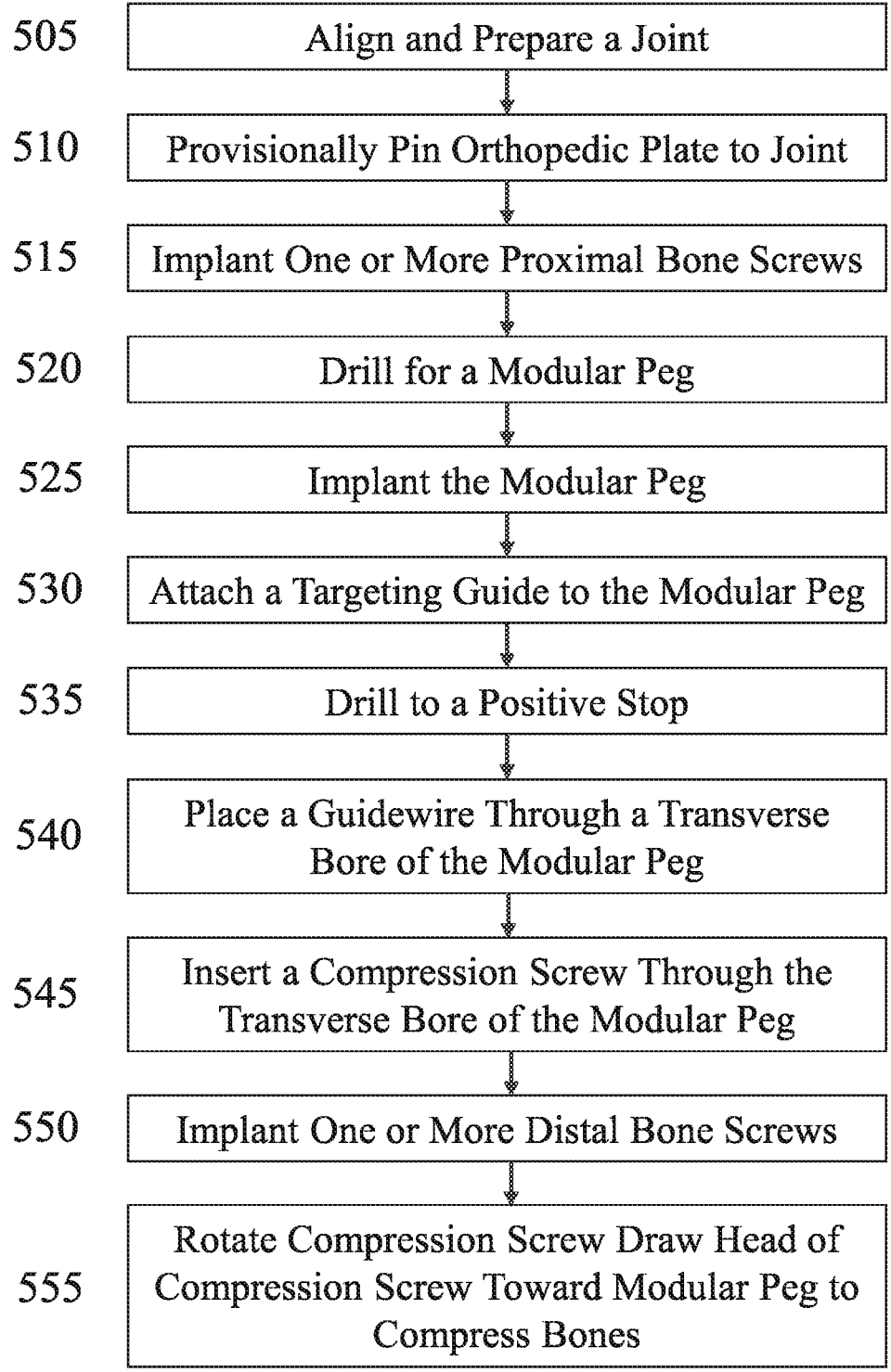
FIG. 11 depicts a method of implantation in accordance with the present invention.

FIG. 11 depicts a method of implanting an assembly comprising an orthopedic plate, bone screws, a modular peg, and a compression screw. At Step 505, the bone or bone fragments to be joined are aligned and prepared. At Step 510, an orthopedic plate is provisionally pinned to the joint or site where the bone or bone fragments meet. The pins may be inserted through one or more apertures intended for bone screws or in smaller apertures in the orthopedic plate. At Step 515, one or more bone screws are implanted into the proximal bone or distal bone. As explained above, at this step, the one or more bone screws may instead be implanted into a distal bone or bone fragment. At Step 520, a hole for a modular peg is drilled in one of the bone or bone fragments. The drill bit may pass through the aperture that will ultimately receive the modular peg. At Step 525, the modular peg is implanted. The top portion of the modular peg may be rotated so that threads on the outer surface of the top portion engage threads within the bore leading from the aperture.

At Step 530, a targeting guide may be attached to the modular peg. For example, as described above, a key insert of the targeting guide may be inserted into an aperture at the top end of the modular peg and may engage a key member of the bottom portion of the modular peg and/or an indentation having the same shape as the key insert. When the targeting guide is coupled to the modular peg, a screw guide of the targeting guide may be aligned with a transverse bore in the modular peg. The targeting guide may be rotated until the transverse bore is angled in a desired direction to receive a compression screw. At Step 535, a hole may be drilled to a positive stop using a drill guide. A depth gauge may be used to measure the desired length of the compression screw. At Step 540, a guidewire such as K-wire may be inserted through the drilled hole and through the transverse bore in the modular peg. A wire guide may be joined to the drill guide to facilitate insertion of the guidewire.

At Step 545, a compression screw may be implanted through one or both of the bones or bone fragments and through a transverse bore of the modular peg. At Step 550, one or more bone screws may be implanted in a distal bone or bone fragment. As explained above, at this step, the one or more bone screws may instead be implanted into a proximal bone or bone fragment. At Step 555, the compression screw may be rotated. As the compression screw is rotated, threads on the shaft of the compressions screw may engage threads in the transverse bore of the modular peg, drawing the head of the compression screw toward the modular peg and thereby compressing the bone or bone fragments.

Figure 12A:
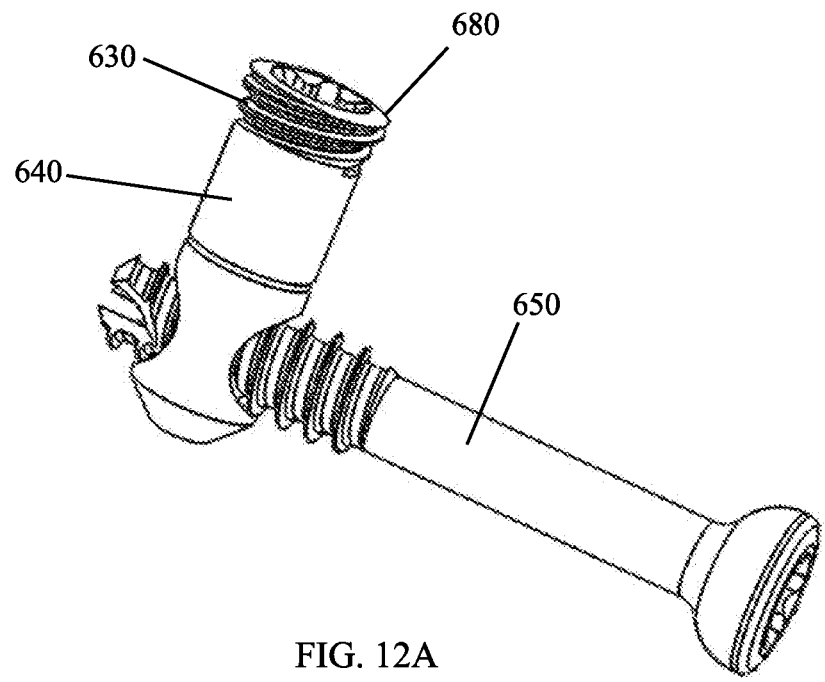
FIGS. 12A and 12B depict side and top views, respectively, of an assembly of a modular peg and a compression screw in accordance with the present invention.
Figure 12B:
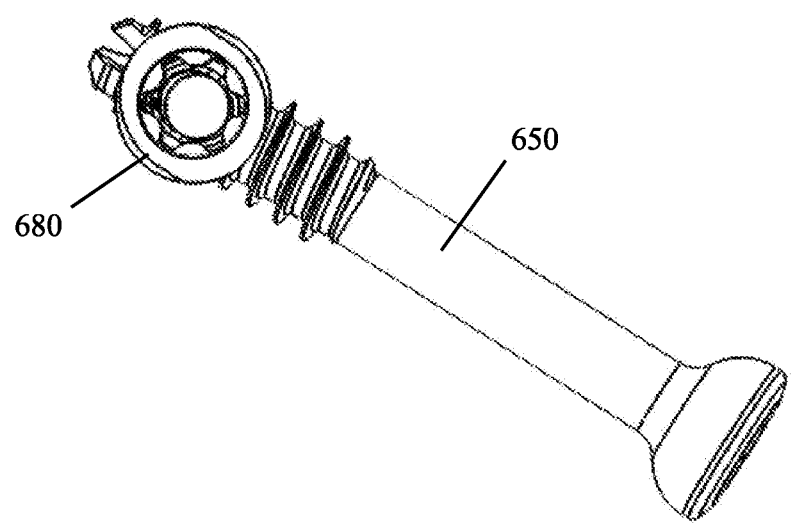
Figure 13:
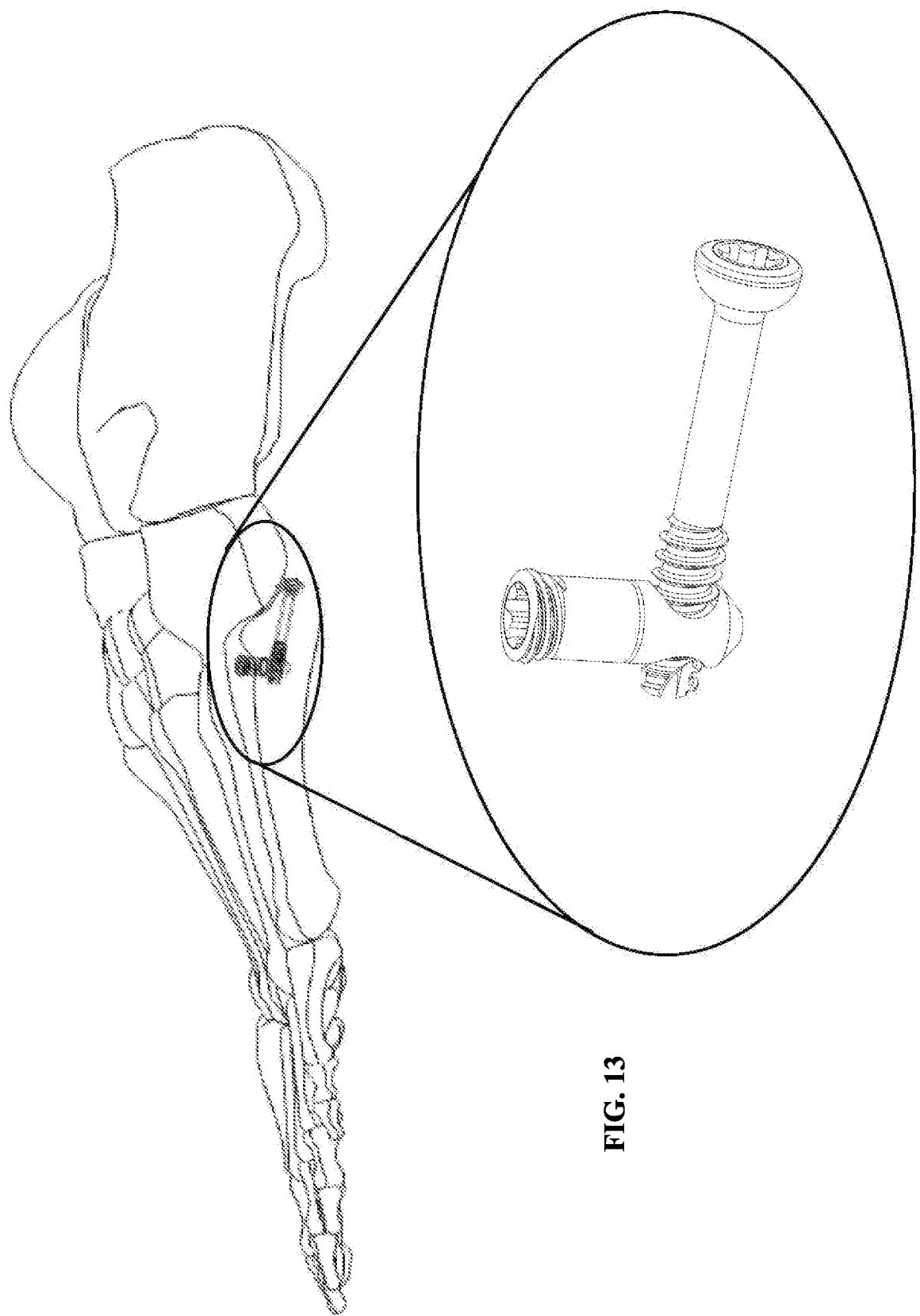
FIG. 13 depicts an assembly used to repair an avulsion fracture, in accordance with the present invention.
Figure 14:
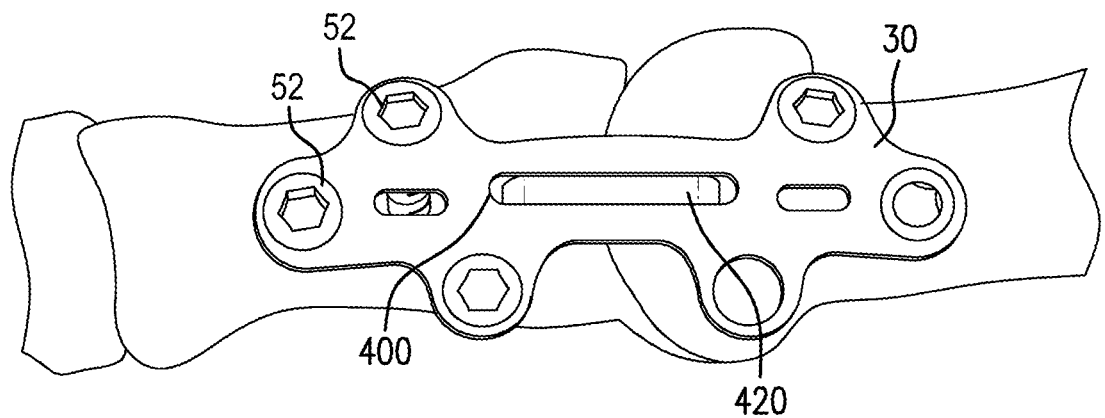
FIG. 14 depicts a top view of an orthopedic plate, bone screws, and a staple in accordance with an embodiment of the present invention.
Figure 15:
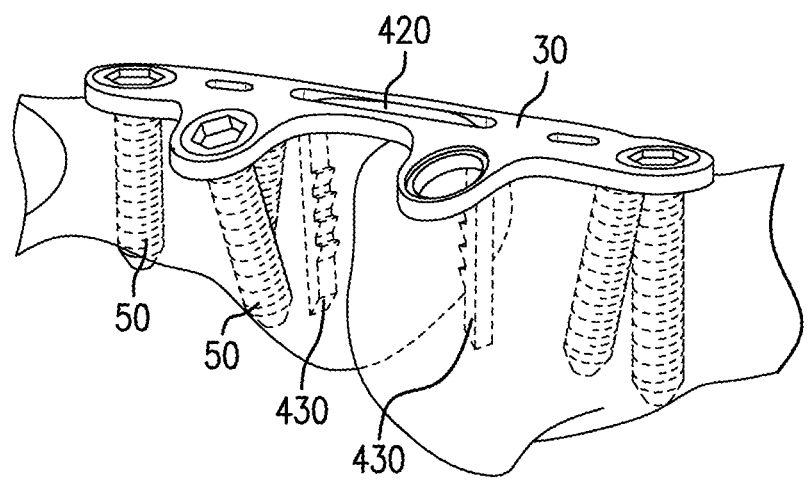
FIG. 15 depicts a perspective view of the orthopedic plate, bone screws, and staple depicted in FIG. 14.

The modular peg and compression screw in accordance with the present invention may also be used to join bones or bone fragments without an orthopedic plate. FIGS. 12A and 12B depict side and top views, respectively, of an assembly of a modular peg (680) and a compression screw (650) in accordance with the present invention. Threads (630) on the exterior surface of top portion (640) of modular peg (680) may be used to implant modular peg (680). Otherwise, the same description for modular peg (80), compression screw (150), and targeting guide (300) would apply to the embodiments shown in FIGS. 12A and 12B. FIG. 13 depicts modular peg (680) and compression screw (650) implanted in a foot to repair an avulsion fracture.

As shown in FIGS. 14-17, a staple (420) may be used with the orthopedic plate (30) in accordance with the present invention. Orthopedic plate (30) may have an indentation (100, 400) capable of receiving a staple (420). Indentation (100, 400) may be aligned with and/or parallel to the longitudinal axis of orthopedic plate (30) or may be offset at an angle from the longitudinal axis.

Figure 16:
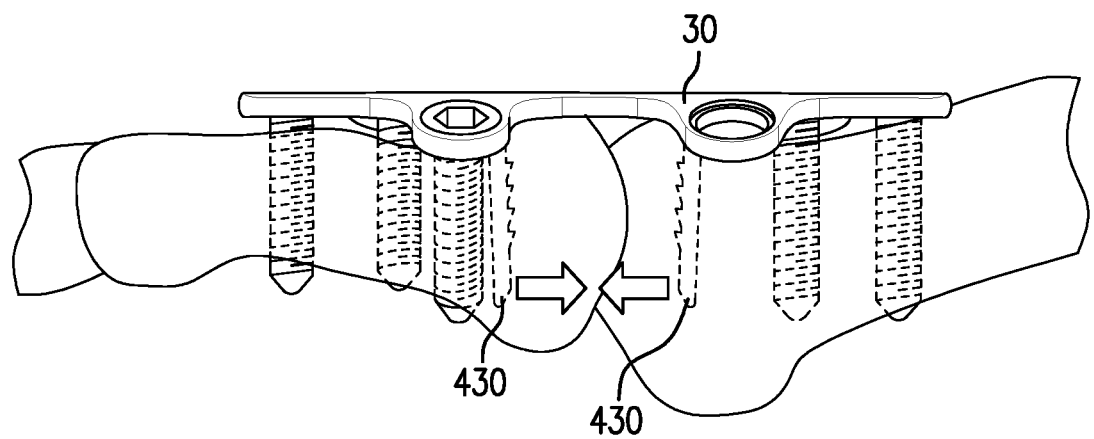
FIG. 16 depicts a side view of the orthopedic plate, bone screws, and staple depicted in FIG. 14.
Figure 17:
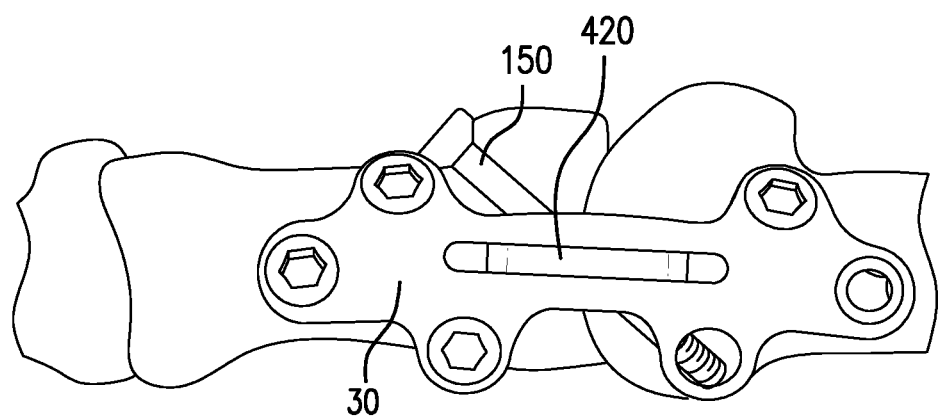
FIG. 17 depicts a top view of an orthopedic plate, bone screws, a compression screw, and a staple in accordance with an embodiment of the present invention.

Staple (420) may have two arms (430). In a resting state, arms (430) may bend toward each other. Before inserting the staple (420) into the bones or bone fragments, arms (430) may be spread apart so that they are, for example, parallel to each other. While the arms (430) are spread apart, they may be inserted into the bones or bone fragment. As shown in FIG. 16, the inclination of the arms (430) to return to their resting state in which they are bent toward each other results in compression of the bone or bone fragments. As indicated in FIG. 17, when compression screw (150) is implanted, it may pass between arms (430) of staple (420).

While the invention has been described with reference to the preferred embodiment and alternative embodiments, which embodiments have been set forth in considerable detail for the purposes of making a complete disclosure of the invention, such embodiments are merely exemplary and are not intended to be limiting or represent an exhaustive enumeration of all aspects of the invention. The scope of the invention, therefore, shall be defined solely by the following claims. Further, it will be apparent to those of skill in the art that numerous changes may be made in such details without departing from the spirit and the principles of the invention. It should be appreciated that the invention is capable of being embodied in other forms without departing from its essential characteristics.

What is claimed is:

1. A system capable of fixating bones or bone fragments comprising:
   an orthopedic plate having a longitudinal plate axis, and a first bore;
   a peg extending along a longitudinal peg axis and comprising a first lower portion rotatably connected to a first upper portion, an outer surfaces of the first upper portion capable of mating with the first bore, the first lower portion comprising a first transverse bore along a first bore axis transverse to and at a first angle about the longitudinal peg axis, wherein an inner surface of the first transverse bore comprises threads;
   a compression screw extending along a longitudinal screw axis, wherein the outer surface comprises screw threads that mate with the threads of the first transverse bore at the first angle and relative to the first longitudinal axis of the orthopedic plate, wherein the first lower portion is configured to be rotated about the longitudinal peg axis to the first angle after mating the first upper portion with the first bore.

2. The system of claim 1, wherein the orthopedic plate further comprises a second bore.

3. The system of claim 2, further comprising a first bone screw having a shaft and a head, wherein the first bone screw couples to the orthopedic plate by being inserted through the second bore, until the exterior surface of the head of the first bone screw abuts the interior surface of the second bore and the threaded portion of the first bone screw extends to engage bone or bone fragment.

4. The system of claim 3, wherein the second bore has the shape of an elongated circle.

5. The system of claim 4, wherein the orthopedic plate further comprises a third bore.

6. The system of claim 5, further comprising a second bone screw having a shaft and a head, wherein the second bone screw couples to the orthopedic plate by being inserted through the third bore until the exterior surface of the head of the second bone screw abuts the interior surface of the third bore and the threaded portion of the second bone screw extends to engage bone or bone fragment.

7. The system of claim 5, further comprising a second peg extending along a second longitudinal peg axis and comprising a second upper portion rotatably connected to a second lower portion, the outer surface of the second upper portion capable of mating with the third bore, the second lower portion comprising a second transverse bore along a second bore axis transverse to and at a second angle about the second longitudinal peg axis, wherein the inner surface of the second transverse bore comprises threads.

8. The system of claim 6, wherein the third bore has the shape of an elongated circle.

9. The system of claim 8, wherein the longitudinal plate axis is parallel to a longitudinal axis of the elongated second bore and elongated third bore are parallel.

10. The system of claim 1, wherein rotating the compression screw brings the head of the compression screw closer to the peg, thereby compressing the bones or bone fragments.

11. The system of claim 1, wherein the first angle about the longitudinal peg axis is perpendicular relative to the longitudinal plate axis.

12. The system of claim 1, wherein the first angle about the longitudinal peg axis is parallel relative to the longitudinal plate axis.

13. They system of claim 1, wherein the first angle about the longitudinal peg axis forms an acute angle relative to the longitudinal plate axis of the orthopedic plate.

14. The system of claim 1, wherein the first bore axis is perpendicular to the longitudinal peg axis.

15. The system of claim 1, wherein the first bore axis is not perpendicular to the longitudinal peg axis.

16. The system of claim 1, wherein the first lower portion comprises a second transverse bore along a second bore axis transverse to and at a second angle about the longitudinal peg axis, wherein the inner surface of the second transverse bore comprises threads.

17. The system of claim 16, further comprising a second a compression screw extending along a second longitudinal screw axis, wherein the outer surface comprises screw threads that mate with the threads of the second transverse bore at the second angle and relative to the first longitudinal axis of the orthopedic plate.

18. The system of claim 17, wherein the second angle relative to the first longitudinal axis of the orthopedic plate is substantially the same as the first angle.

19. The system of claim 17, wherein the second angle relative to the first longitudinal axis of the orthopedic plate is different than that of the first angle.

* * * * *